United States Patent
Herrmann et al.

(10) Patent No.: US 10,870,007 B2
(45) Date of Patent: Dec. 22, 2020

(54) CARDIAC DEVICE ACCLIMATION PROFILE

(71) Applicant: Cardiac Pacemakers, Inc., St. Paul, MN (US)

(72) Inventors: Keith L. Herrmann, Minneapolis, MN (US); Stephen J. Hahn, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 125 days.

(21) Appl. No.: 15/791,594

(22) Filed: Oct. 24, 2017

(65) Prior Publication Data

US 2018/0126171 A1    May 10, 2018

Related U.S. Application Data

(60) Provisional application No. 62/419,635, filed on Nov. 9, 2016.

(51) Int. Cl.
*A61N 1/36* (2006.01)
*A61N 1/365* (2006.01)
(Continued)

(52) U.S. Cl.
CPC ......... *A61N 1/36507* (2013.01); *A61N 1/056* (2013.01); *A61N 1/365* (2013.01); *A61N 1/3702* (2013.01); *A61N 1/37235* (2013.01)

(58) Field of Classification Search
USPC ........................................................ 607/17
See application file for complete search history.

(56) References Cited

U.S. PATENT DOCUMENTS

| 4,945,909 A | 8/1990 | Fearnot et al. |
| 5,226,413 A | 7/1993 | Bennett et al. |

(Continued)

FOREIGN PATENT DOCUMENTS

| CN | 109963612 A | 7/2019 |
| WO | WO-2018089191 A1 | 5/2018 |

OTHER PUBLICATIONS

"International Application Serial No. PCT/US2017/058139, International Preliminary Report on Patentability dated May 23, 2019", 7 pgs.

(Continued)

*Primary Examiner* — Nicole F Lavert
(74) *Attorney, Agent, or Firm* — Schwegman Lundberg & Woessner, P.A.

(57) ABSTRACT

This document discusses, among other things, systems and methods to acclimate a patient to therapy from an implantable medical device. For instance, an implantable medical device can include pulse generation circuitry, sensing circuitry, and a controller. The pulse generation circuitry can generate electrical pulses. The sensing circuitry can be for sensing cardiac electrical activity of the patient. In an example, the controller can detect cardiac events that define pacing timing intervals and control the delivery of electrical pulses in accordance with a programmed mode. The controller can be programmed to provide instructions to the pulse generation circuitry to deliver electrical pulses to the heart of a patient. In an example, the electrical pulses can be based on a therapy parameter. The controller can be configured to adjust the therapy parameter according to an acclimation profile to acclimate the patient to a stimulation therapy.

18 Claims, 6 Drawing Sheets

(51) Int. Cl.
  *A61N 1/37* (2006.01)
  *A61N 1/05* (2006.01)
  *A61N 1/372* (2006.01)

(56) References Cited

U.S. PATENT DOCUMENTS

| | | |
|---|---|---|
| 5,725,561 A | 3/1998 | Stroebel et al. |
| 5,814,087 A | 9/1998 | Renirie |
| 5,861,011 A | 1/1999 | Stoop |
| 7,577,479 B2 | 8/2009 | Hartley et al. |
| 8,175,708 B1 | 5/2012 | Snell et al. |
| 2002/0165586 A1 | 11/2002 | Hill et al. |
| 2003/0093122 A1 | 5/2003 | Vanhout |
| 2004/0260348 A1 | 12/2004 | Bakken et al. |
| 2007/0239037 A1 | 10/2007 | Ghio et al. |
| 2008/0081958 A1 | 4/2008 | Denison et al. |
| 2014/0277256 A1 | 9/2014 | Osorio |
| 2015/0306401 A1* | 10/2015 | Demmer ............ A61B 5/04525 600/519 |
| 2015/0321011 A1* | 11/2015 | Carney .............. A61N 1/36514 607/62 |
| 2016/0129259 A1* | 5/2016 | Libbus .................. G16H 20/40 607/59 |

OTHER PUBLICATIONS

"International Application Serial No. PCT/US2017/058139, International Search Report dated Jan. 22, 2018", 5 pgs.
"International Application Serial No. PCT/US2017/058139, Written Opinion dated Jan. 22, 2018", 5 pgs.
"European Application Serial No. 17794605.0, Communication Pursuant to Article 94(3) EPC dated Jul. 20, 2020", 5 pgs.

* cited by examiner

CARDIAC DEVICE ACCLIMATION PROFILE

CLAIM OF PRIORITY

This application claims the benefit of priority under 35 U.S.C. § 119(e) of U.S. Provisional Patent Application Ser. No. 62/419,635, filed on Nov. 9, 2016, which is herein incorporated by reference in its entirety.

TECHNICAL FIELD

This document relates generally to medical devices, and more particularly, but not by way of limitation, to systems, devices, and methods to gradually introduce cardiac therapy.

BACKGROUND

Implantable medical devices, such as implantable cardioverter defibrillator (ICD) or cardiac rhythm management (CRM) devices, can be used to monitor, detect, or treat various cardiac conditions that can result in a reduced ability of a heart to sufficiently deliver blood to a body. In some cases, heart conditions may lead to rapid, irregular, or inefficient heart contractions, etc. To alleviate one or more of these conditions, various medical devices can be implanted in a patient's body to monitor heart activity or to provide electrical stimulation to optimize or control contractions of the heart.

Some patients, such as those having conditions such as bradycardia, chronotropic incompetence (C.I.), or the like, can develop lower than normal intrinsic heart rates. Further, the heart rate during activity and the maximum heart rate for some of these patients may be lower than normal as well. Treatment for patients with abnormal intrinsic heart rates, such as those described above, often includes installation of an implantable medical device for pacing the heart.

SUMMARY

This document discusses, among other things, systems and methods to gradually introduce stimulation therapy to a patient with an implantable medical device, such as an implantable medical device operating in according with an acclimation profile for gradually introducing the stimulation therapy to the patient.

Example 1 is a method of operating a cardiac device, comprising: initiating delivery of a stimulation therapy to a heart of a patient, the stimulation therapy including delivering electrical pulses to a heart of a patient based on a therapy parameter; and adjusting the therapy parameter according to an acclimation profile to acclimate the patient to the delivery of the stimulation therapy.

In Example 2, the subject matter of Example 1 optionally includes wherein the acclimation profile includes adjusting the therapy parameter from a starting parameter value to a target parameter value over an acclimation period.

In Example 3, the subject matter of Example 2 optionally includes wherein adjusting the therapy parameter includes adjusting the therapy parameter from the starting parameter value to the target parameter value along the acclimation profile linearly.

In Example 4, the subject matter of any one or more of Examples 1-3 optionally include wherein adjusting the therapy parameter includes adjusting at least one of the starting parameter value and the target parameter value are based on a percentage of the therapy parameter.

In Example 5, the subject matter of any one or more of Examples 1-4 optionally include adjusting a second therapy parameter based on a second acclimation profile having a second starting parameter value and a second target parameter value.

In Example 6, the subject matter of any one or more of Examples 1-5 optionally include wherein adjusting the therapy parameter includes adjusting the therapy parameter based on a daytime acclimation profile segment and a nighttime acclimation profile segment, the daytime acclimation profile segment having a therapy parameter corresponding to a faster cardiac rhythm than the nighttime acclimation profile segment.

In Example 7, the subject matter of any one or more of Examples 1-6 optionally include adjusting the therapy parameter during an acclimation period that extends for at least 12 hours.

In Example 8, the subject matter of any one or more of Examples 1-7 optionally include wherein adjusting the therapy parameter includes adjusting a lower rate limit of a cardiac rhythm.

In Example 9, the subject matter of any one or more of Examples 1-8 optionally include wherein adjusting the therapy parameter includes adjusting a maximum tracking rate of a cardiac rhythm.

In Example 10, the subject matter of any one or more of Examples 1-9 optionally include wherein adjusting the therapy parameter includes adjusting a rate response factor, the rate response factor is a rate at which a cardiac rhythm is adjusted by the pulse generation circuitry.

Example 11 is an implantable medical device comprising means for performing any of the methods of Examples 1-10.

Example 12 is at least one machine-readable medium including instructions, which when executed by a machine, cause the machine to perform operations of any of the methods of Examples 1-10.

Example 13 is an implantable medical device comprising: pulse generation circuitry for generating electrical pulses; sensing circuitry for sensing cardiac electrical activity; and a controller for detecting cardiac events that define pacing timing intervals and for controlling the delivery of electrical pulses in accordance with a programmed mode, wherein the controller is programmed to: provide instructions to the pulse generation circuitry to deliver electrical pulses to the heart of a patient, the electrical pulses based on a therapy parameter, wherein the controller is configured to adjust the therapy parameter according to an acclimation profile to acclimate the patient to a stimulation therapy.

In Example 14, the subject matter of Example 13 optionally includes wherein the acclimation profile includes a starting parameter value and a target parameter value, wherein the therapy parameter is adjusted from the starting parameter value to the target parameter value over an acclimation period.

In Example 15, the subject matter of any one or more of Examples 13-14 optionally include wherein the therapy parameter is a lower rate limit of a cardiac rhythm.

Example 16 is a method of operating a cardiac device, comprising: initiating delivery of a stimulation therapy to a heart of a patient, the stimulation therapy including delivering electrical pulses to a heart of a patient based on a therapy parameter; and adjusting the therapy parameter according to an acclimation profile to acclimate the patient to the delivery of the stimulation therapy.

In Example 17, the subject matter of Example 16 optionally includes wherein the acclimation profile includes adjusting the therapy parameter from a starting parameter value to a target parameter value over an acclimation period.

In Example 18, the subject matter of Example 17 optionally includes wherein adjusting the therapy parameter includes adjusting the therapy parameter from the starting parameter value to the target parameter value along the acclimation profile linearly.

In Example 19, the subject matter of any one or more of Examples 17-18 optionally include wherein adjusting the therapy parameter includes adjusting at least one of the starting parameter value and the target parameter value are based on a percentage of the therapy parameter.

In Example 20, the subject matter of any one or more of Examples 17-19 optionally include adjusting a second therapy parameter based on a second acclimation profile having a second starting parameter value and a second target parameter value.

In Example 21, the subject matter of any one or more of Examples 16-20 optionally include wherein adjusting the therapy parameter includes adjusting the therapy parameter based on a daytime acclimation profile segment and a nighttime acclimation profile segment, the daytime acclimation profile segment having a therapy parameter corresponding to a faster cardiac rhythm than the nighttime acclimation profile segment.

In Example 22, the subject matter of any one or more of Examples 16-21 optionally include adjusting the therapy parameter during an acclimation period that extends for at least 12 hours.

In Example 23, the subject matter of any one or more of Examples 16-22 optionally include wherein adjusting the therapy parameter includes adjusting a lower rate limit of a cardiac rhythm.

In Example 24, the subject matter of any one or more of Examples 16-23 optionally include wherein adjusting the therapy parameter includes adjusting a maximum tracking rate of a cardiac rhythm.

In Example 25, the subject matter of any one or more of Examples 16-24 optionally include wherein adjusting the therapy parameter includes adjusting a rate response factor, the rate response factor is a rate at which a cardiac rhythm is adjusted by the pulse generation circuitry.

Example 26 is an implantable medical device comprising: pulse generation circuitry for generating electrical pulses; sensing circuitry for sensing cardiac electrical activity; and a controller for detecting cardiac events that define pacing timing intervals and for controlling the delivery of electrical pulses in accordance with a programmed mode, wherein the controller is programmed to: provide instructions to the pulse generation circuitry to deliver electrical pulses to the heart of a patient, the electrical pulses based on a therapy parameter, wherein the controller is configured to adjust the therapy parameter according to an acclimation profile to acclimate the patient to a stimulation therapy.

In Example 27, the subject matter of Example 26 optionally includes wherein the acclimation profile includes a starting parameter value and a target parameter value, wherein the therapy parameter is adjusted from the starting parameter value to the target parameter value over an acclimation period.

In Example 28, the subject matter of Example 27 optionally includes wherein the acclimation profile is linear from the starting parameter value to the target parameter value.

In Example 29, the subject matter of any one or more of Examples 27-28 optionally include wherein the therapy parameter includes is a rate response factor, the rate response factor being a rate at which a cardiac rhythm is adjusted by the pulse generation circuitry, and the acclimation profile includes an adjustment to the rate response factor over the acclimation period.

In Example 30, the subject matter of any one or more of Examples 27-29 optionally includes the acclimation period lasting for at least 12 hours.

In Example 31, the subject matter of any one or more of Examples 26-30 optionally include wherein the controller is further programmed to adjust a second therapy parameter according to a second acclimation profile.

In Example 32, the subject matter of any one or more of Examples 26-31 optionally include wherein the acclimation profile includes a daytime acclimation profile segment and a nighttime acclimation profile segment, the daytime acclimation profile segment having a therapy parameter corresponding to a faster cardiac rhythm than the nighttime acclimation profile segment.

In Example 33, the subject matter of any one or more of Examples 26-32 optionally include wherein at least one of the starting parameter and the target parameter are based on a percentage of the therapy parameter.

In Example 34, the subject matter of any one or more of Examples 26-33 optionally include wherein the therapy parameter is a lower rate limit of a cardiac rhythm.

In Example 35, the subject matter of any one or more of Examples 26-34 optionally include wherein the therapy parameter is a maximum tracking rate of a cardiac rhythm.

In Example 36 a system or apparatus may optionally combine any portion or combination of any portion of any one or more of Examples 1-35 to include "means for" performing any portion of any one or more of the functions or methods of Examples 1-35, or a "machine-readable medium" (e.g., massed, non-transitory, etc.) including instructions that, when performed by a machine, cause the machine to perform any portion of any one or more of the functions or methods of Examples 1-35.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
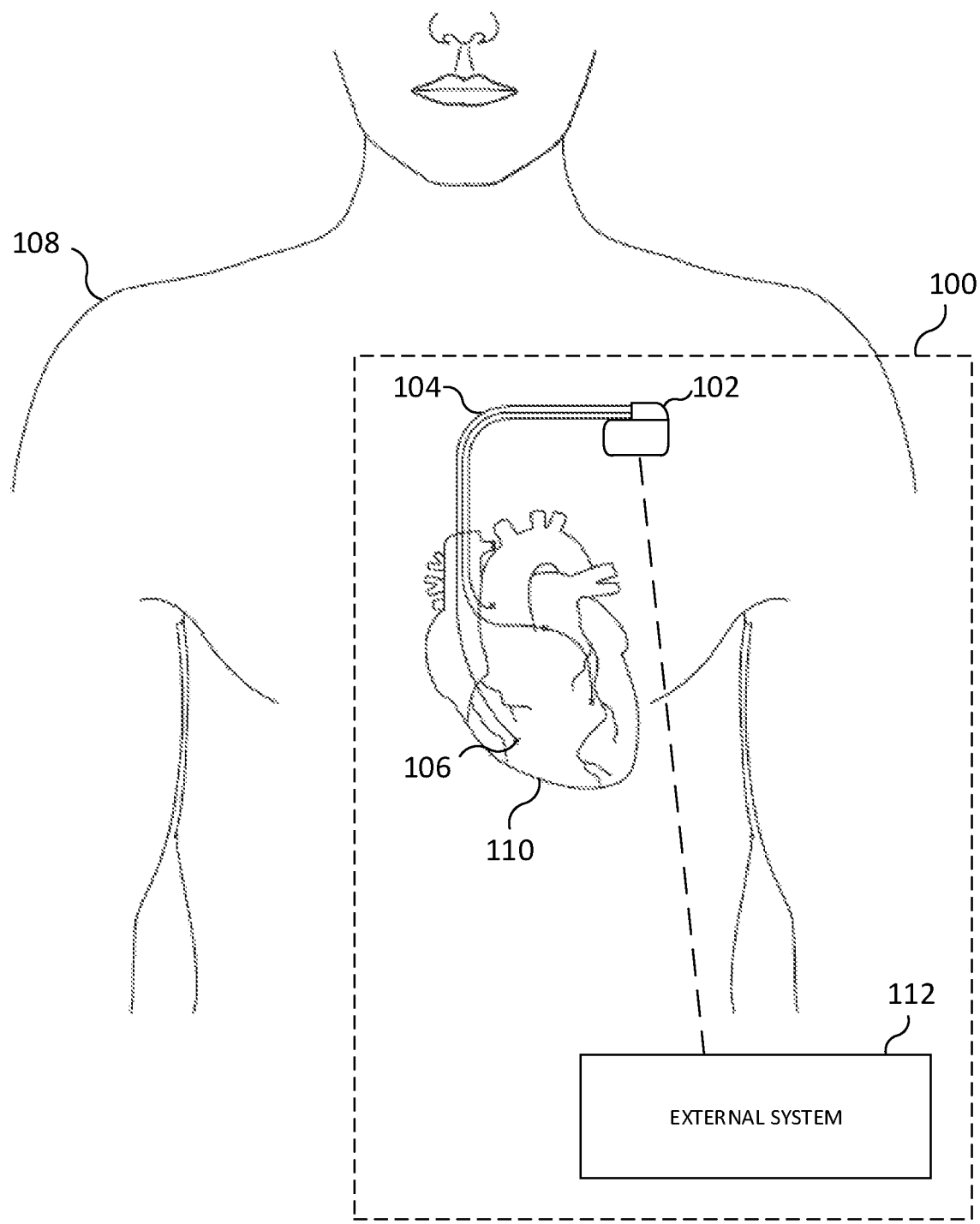
FIG. 1 illustrates an example system including an implantable medical device, according to an embodiment.

Patients with certain heart conditions may have abnormal intrinsic heart rates. For instance, patients with such conditions, such as sick sinus syndrome, bradycardia, and chronotropic incompetence (C.I.), or the like, can become accustomed to having lower intrinsic heart rates, such as 45 beats per minute (BPM), 35 BPM, or lower. Further, the maximum heart rate for some of these patients may be as low as 70 to 90 BPM. Treatment for patients with abnormal intrinsic heart rates, such as those described above, often includes installation of an implantable medical device for pacing the heart, such as a pacemaker (e.g. implantable cardioverter defibrillator (ICD) or cardiac resynchronization therapy device). In operation, implantable medical devices can monitor and manage the cardiac rhythm of the patient, including increasing the heart rate of the patient to a non-symptomatic rate (e.g. anti-bradycardia pacing) or providing cardiac resynchronization therapy (CRT). For example, the implantable medical device can maintain a lower rate limit (LRL) of the patient at 60 BPM and a maximum tracking rate (MTR) of 130 BPM. Settings (e.g., therapy parameters) of the implantable medical device can be programmed prior to insertion of the device. In some instances, the therapy parameters can be programmed after installation by a physician. For instance, the physician can program the implantable medical device using a specialized wand for communicating with the circuitry of the device or using a secure wireless connection (e.g., MICS telemetry). Following installation of the implantable medical device, the patient may feel discomfort related to the increased heart rate associated with the treatment, especially when trying to sleep at night. For instance the patient may be alarmed or distressed by an increased heart rate maintained by the implantable device, e.g., at a LRL that is higher than a low intrinsic rate to which the patient has become accustomed.

The present inventors have recognized, among other things, that an implantable medical device having an acclimation profile for providing stimulation therapy to a patient can gradually introduce the stimulation therapy to the patient. For instance, a gradually-introduced stimulation therapy can be less distressing for a patient with a recently implanted medical device.

In some examples, an acclimation profile can be programmed into an implantable medical device that is configured to affect a heart, such as a pacemaker. The implantable medical device can include pulse generation circuitry for generating electrical pulses and sensing circuitry for sensing cardiac electrical activity. The cardiac device can further include a controller for detecting cardiac events that define pacing timing intervals and for controlling the delivery of electrical pulses in accordance with a programmed mode. The controller can be programmed to deliver electrical pulses to the heart of a patient. The electrical pulses can be based on the therapy parameter. For example, where the implantable medical device performs cardiac pacing or CRT, the therapy parameter can include the LRL, MTR, or a rate response factor (RRF). The pulse generation circuitry can be configured to adjust the therapy parameter according to an acclimation profile to acclimate the patient to the stimulation therapy. Accordingly, initial discomfort and distress related with the therapy parameter can be reduced by the acclimation profile. Adjusting therapy parameters often requires a trip to the physician for diagnosis of the issue and reprogramming using specialized equipment. Scheduling visits can be difficult for certain patients with reduced mobility, can create additional workload for the physician, increased costs for the patient and the healthcare system in general, and can prolong patient discomfort as a result of waiting for a scheduled appointment. In some examples, the acclimation profile of the present disclosure can be programmed into the implantable medical device before insertion into the patient, thereby mitigating visits to the physician and additional reprogramming. In a further example, the acclimation profile can be programmed into the implantable medical device after insertion into the patient and can accordingly mitigate additional visits to the physician for additional reprogramming.

In an example, the acclimation profile can include a starting parameter value and a target parameter value. The therapy parameter can be adjusted from the starting parameter value to the target parameter value over an acclimation period. In an example, the starting parameter and the target parameter can be based on a percentage of the therapy parameter. In some examples, the acclimation period can be less than one day, two days, one week, two weeks, one month, several months, or the like. In a further example, the acclimation period can be at least 12 hours, such as between 12 hours and 48 hours. In another example, the acclimation profile can include a daytime acclimation profile segment and a nighttime acclimation profile segment. For instance, patients may experience greater discomfort associated with the stimulation therapy at nighttime, where a heart rate that is faster (e.g., noticeably faster) than the patient is accustomed. This can be alarming or distressing and can disrupt or inhibit sleep. Accordingly, the therapy parameter of the nighttime acclimation profile segment can correspond to a slower cardiac rhythm than the daytime profile. In this manner, the stimulation therapy can accommodate a naturally slower resting heart rate during sleep according to the acclimation profile. In a further example, the controller can be further programmed to adjust a second therapy parameter according to a second acclimation profile. For instance, the controller can adjust the first therapy parameter and the second therapy parameter based on one or more acclimation profiles. The first and second acclimation profiles can be performed on the first and second therapy parameter respectively or more than one acclimation profile can be applied to one therapy parameter.

FIG. 1 illustrates an example system 100 including an implantable medical device 102, according to an embodiment. In some examples, the implantable medical device can include a cardiac pacing device (i.e. pacemaker), cardiac resynchronization therapy (CRT) device, monitoring or sensory device that can optionally deliver therapy, neurostimulation device, leadless pacemaker, or other device. As shown in the example of FIG. 1, the implantable medical device 102 can include a cardiac device that is configured to deliver a pacing pulse (e.g., a pacemaker ICD with pacing capability or CRT device). The implantable medical device 102 can be coupled to at least one lead 104. The lead 104 can include an electrical conductor, such as a wire. An electrode 106 can be positioned on the lead 104, such as at a distal end of the lead 104. The lead 104 can deliver electrical pulses from the implantable medical device 102 to the electrode 106. The electrical pulses can be delivered to a patient 108 for stimulation therapy. For instance, the implantable medical device 102 can deliver the electrical pulses to a heart 110 of the patient 108 to provide stimulation therapy, such as pacing, CRT, defibrillation, or the like. In an example, the electrode 106 can be located in the heart 108, such as in the right atrium, right ventricle, left ventricle, left atrium, or other location in or on the heart 108. In a further example, the implantable medical device 102 can be communicatively coupled to an external device or system 112, such as a clinician programmer or patient communicator. The external system 112 can transmit therapy parameters to the implantable medical device 102 or receive sensory data collected by the implantable medical device 102. In an example, the external system 112 can facilitate programming of the implantable medical device 102. For instance, the external system 112 can transmit a wireless command to program the implantable medical device 102 according to an acclimation profile.

Figure 2:
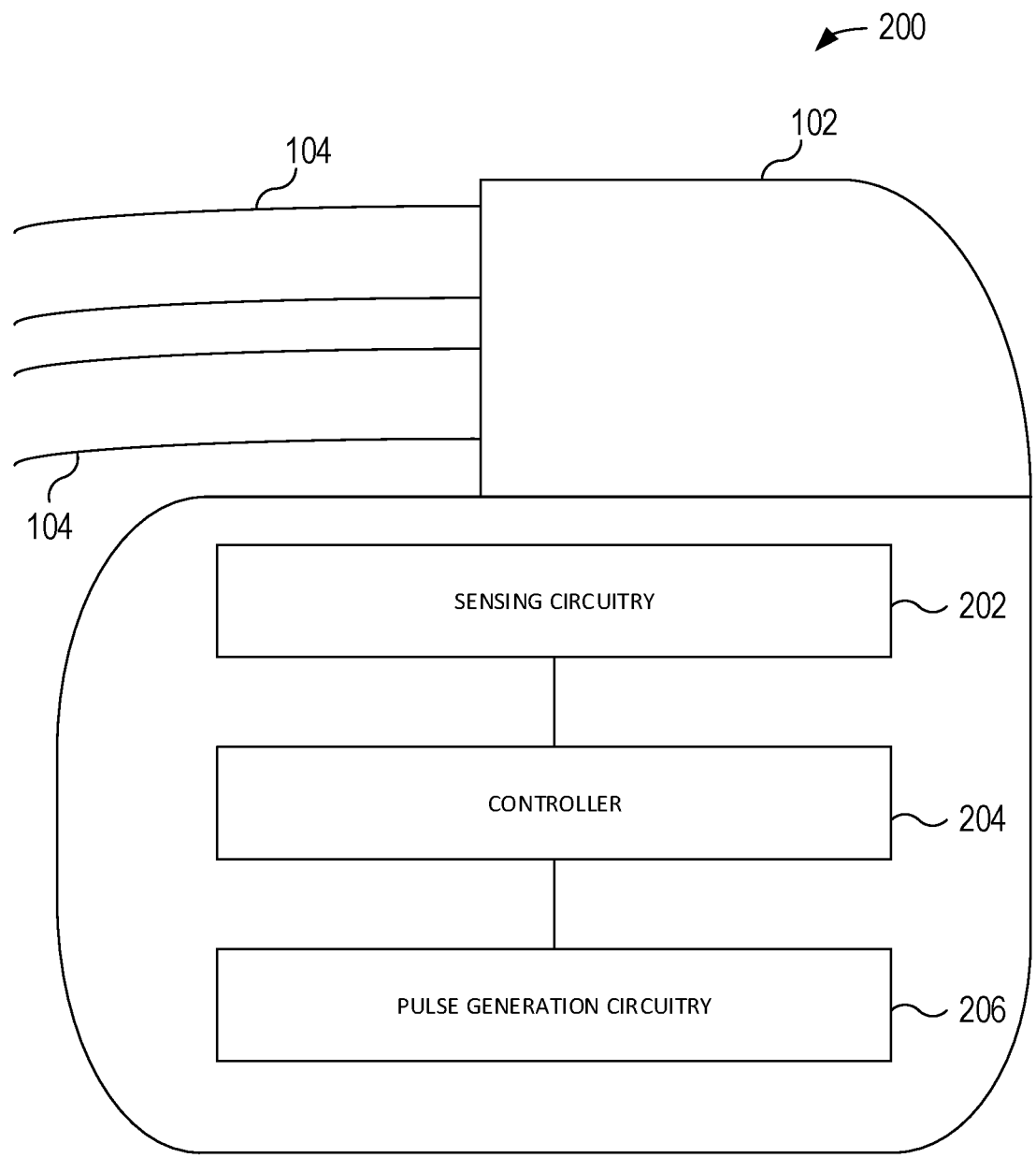
FIG. 2 illustrates a system diagram of an example of an implantable medical device, according to an embodiment.

FIG. 2 illustrates a system diagram 200 of an example of the implantable medical device 102. The implantable medical device 102 can include sensing circuitry 202, a controller 204, and pulse generation circuitry 206. In an example, the sensing circuitry 202 can detect physiological characteristics of the patient 108. In some examples, the sensory circuitry 202 can be communicatively coupled to an electrical sensor, pressure transducer, temperature sensor, acoustic transducer, activity sensor or accelerometer, or other sensor. Accordingly, the sensing circuitry 202 can detect physiological characteristics to monitor the patient for treatable symptoms, such as bradycardia, sick sinus syndrome, CI, or the like.

The controller 204 can receive the signals relating to physiological characteristics from the sensing circuitry 202. Based on the physiological characteristics, the controller 204 can detect a cardiac event or physiologic condition. The cardiac event can include, but is not limited to, a P wave, QRS wave, other cardiac electrical activity, or the like. Other physiologic characteristics can include a change in temperature, breathing (e.g., respiration rate, minute ventilation (MV)), activity level, fluid status (e.g. edema), or the like. In some examples, such physiological characteristics can affect cardiac performance or demand for cardiac output. The controller 204 can initiate the delivery of electrical pulses based on a pacing timing interval (a time interval between electrical pulses of the stimulation therapy), a detected cardiac event, or both in accordance with a programmed mode. In various examples, the programmed mode can include, but is not limited to, a bradycardia therapy mode (e.g., pacing mode), rate responsive therapy (e.g. pacing responsive to intrinsic activity, combined with a lower rate limit), sensor-driven pacing therapy (e.g. responsive to activity or respiration), a CRT mode (e.g. pacing both the left and right side of the heart to promote synchronization), or other modes, and various combinations thereof. The controller 204 can be programmed to communicate with the pulse generation circuitry 206 to initiate delivery of the electrical pulses based on a therapy parameter, such as the LRL, MTR, RRF, or other therapy parameter. The controller can be configured to adjust the therapy parameter according to an acclimation profile to acclimate the patient to the stimulation therapy. In various examples, the controller 204 can include, but is not limited to, a processor having instructions stored thereon to command the pulse generation circuitry 206 to deliver the electrical pulses. In various examples, the instructions can be stored in memory of the processor or in a separate memory package that is communicatively coupled with the processor. In a further example, the controller 204 can be programmed to communicate with the pulse generation circuitry 206 to initiate delivery of the electrical pulses based on a second therapy parameter, such as the LRL, MTR, RRF, or the like.

In operation, the pulse generation circuitry 206 can produce at least one electrical pulse for delivery to the patient. For instance, the controller 204 can provide instructions to the pulse generation circuitry 206 to deliver the electrical pulse to the heart of the patient based on the therapy parameter. The pulse generation circuitry 206 can produce an electrical pulse having various amplitudes, frequencies, burst frequencies, pulse widths, or various waveforms. Accordingly, the electrical pulse can be delivered from the pulse generation circuitry 206 to the one or more leads. The electrical pulse can be transmitted through the lead, into the electrode, and to the patient. In an example, such as the example of FIG. 1, the electrical pulse can be transmitted to the heart 108, such as to the right atrium, right ventricle, left ventricle, left atrium, or other location on the heart 108. Leadless configurations are also possible, such as examples where an electrode is coupled to or integrated into the housing of an implantable device.

Figure 3:
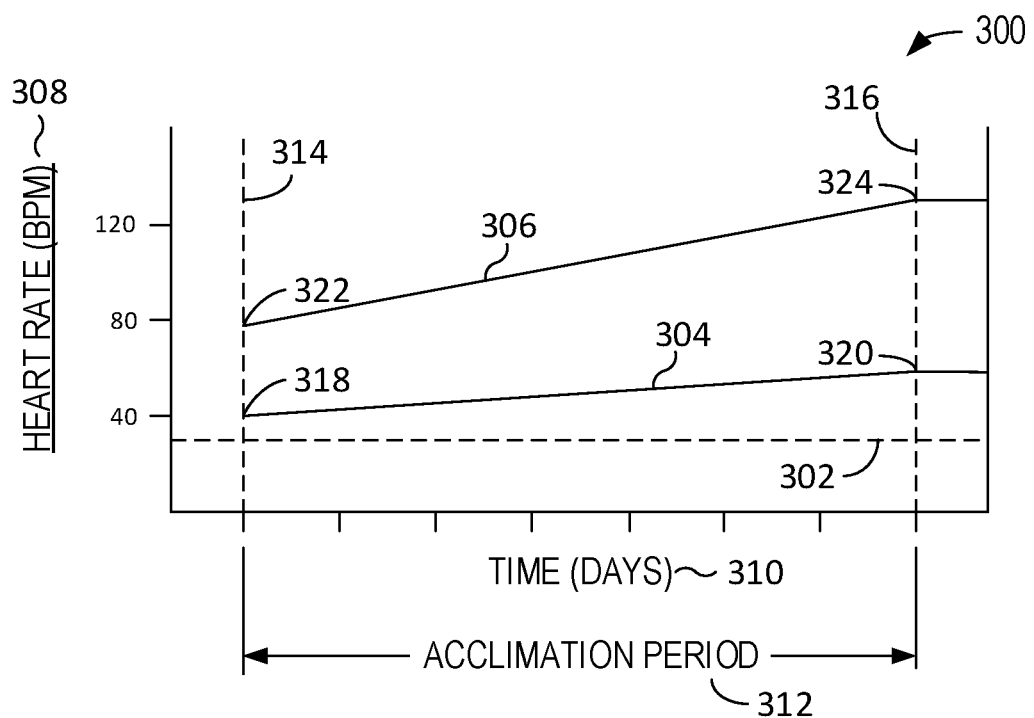
FIG. 3 illustrates an example of a chart depicting an acclimation profile.

FIG. 3 illustrates an example of a chart 300 depicting the acclimation profile. The acclimation profile can gradually introduce the stimulation therapy to the patient. For instance, patients with bradycardia can be accustomed to living with an abnormally low intrinsic heart rate 302, such as thirty-five to forty-five beats-per-minute. In an example, stimulation therapy for bradycardia can include setting an LRL (lower rate limit, e.g., a parameter to define a minimum allowable heart rate) of sixty beats-per-minute. Following insertion of the implantable medical device 102 into the patient 108, the stimulation therapy can feel abnormal or alarming to the patient 108 in some instances. The acclimation profile can reduce the abnormal or alarming feeling of the patient related to the stimulation therapy, for instance by gradually shifting the paced rate to an target increased heart rate based on a prescribed adjustment of the pacing timing interval (e.g., established by the LRL).

In the example of FIG. 3, the acclimation profile can be implemented on the cardiac device, such as the implantable medical device 102. For instance, the chart 300 includes a horizontal axis depicting time 310 and a vertical axis depicting heart rate 308 in beats per minute (BPM). The acclimation profile can be implemented over an acclimation period 312. The acclimation period 312 can be a duration of time between a starting time 314 and a completion time 316. For instance, the starting time 314 can correspond with the insertion of the implantable medical device 102 or the initiation of the stimulation therapy. The completion time 316 can correspond to a time when the acclimation period 312 has elapsed and the stimulation therapy is delivered based on target parameters (e.g., the stimulation therapy parameters prescribed by a physician). In various examples, the acclimation period 312 can include less than one-day, one day, two days, one week, two weeks, one month, or any period in between. In a further example, the acclimation period can be at least 12 hours, such as between 12 hours and 48 hours.

The example of FIG. 3 illustrates a first acclimation profile 304 and a second acclimation profile 306. In the example shown, the therapy parameter of the first acclimation profile 304 is the LRL, and a second therapy parameter of the second acclimation profile 306 is the MTR. For instance, the first acclimation profile 304 can establish the minimum allowable heart rate and the second acclimation profile 306 can establish the maximum allowable heart rate.

The acclimation profile, such as acclimation profile 304 or 306, can include a starting parameter value, such as starting parameter value 318 or 322, and a target parameter value, such as target parameter value 320 or 324. The starting parameter value can correspond to the therapy parameter value at the starting time 314, and the target parameter value can correspond to the therapy parameter value at the completion time 316. The therapy parameter can be adjusted from the starting parameter value to the target parameter value over the acclimation period 312. The therapy parameter values of the acclimation profile 306 can be greater than the therapy parameter values of acclimation profile 304 as the MTR corresponds to greater heart rate than the LRL. In the example of FIG. 3, the acclimation profile 304 (e.g., LRL value) has a starting parameter value 318 of forty BPM and increases linearly over the acclimation period 312 to a target parameter value 320 of sixty-five BPM. The acclimation profile 306 (e.g., MTR value) can have a starting parameter value 322 of eighty BPM and increase linearly over the acclimation period 312 to a target parameter value 324 of one-hundred and thirty BPM. The starting parameter value and the target parameter value can be based on fixed values as described in the example above. In another example, at least one of the starting parameter value or the target parameter value can be based on a percentage. For instance, the starting parameter value 322 can be based on a percentage of the target parameter value 324. The percentage can increase from the starting parameter value 322 to the target parameter value 324 over the acclimation period 312 until the stimulation therapy is delivering the target parameter value 324. While the acclimation profiles illustrated in FIG. 3 are linear, the acclimation profile of LRL, MTR or another parameter can alternatively be specified according to a non-linear function, such as an exponential, logarithmic, or other profile shape.

In a further example, the therapy parameter can be the rate response factor (RRF). The RRF can be a rate at which the heart rate is adjusted by the pulse generation circuitry, such as pulse generation circuitry 206. The acclimation profile can adjust the RRF over the acclimation period 312. For instance, the RRF can be based on a sensed physiology parameter (e.g., detected by the sensing circuitry 202) and can increase or decrease the pacing rate corresponding to the physiological parameter. In an example, when the sensing circuitry 202 detects an increase activity level (e.g., based on increase movement detected by an accelerometer, increased temperature, increased breathing rate, or the like), then, the RRF can be applied to the therapy parameter prescribed by the acclimation profile to control the heart rate of the patient based on the detected activity level. Used in this way, the patient can gradually receive increasing pacing rates for a given amount of activity (e.g., MV of the like) while allowing the physician to independently control the LRL, MTR, or other parameter.

Figure 4:
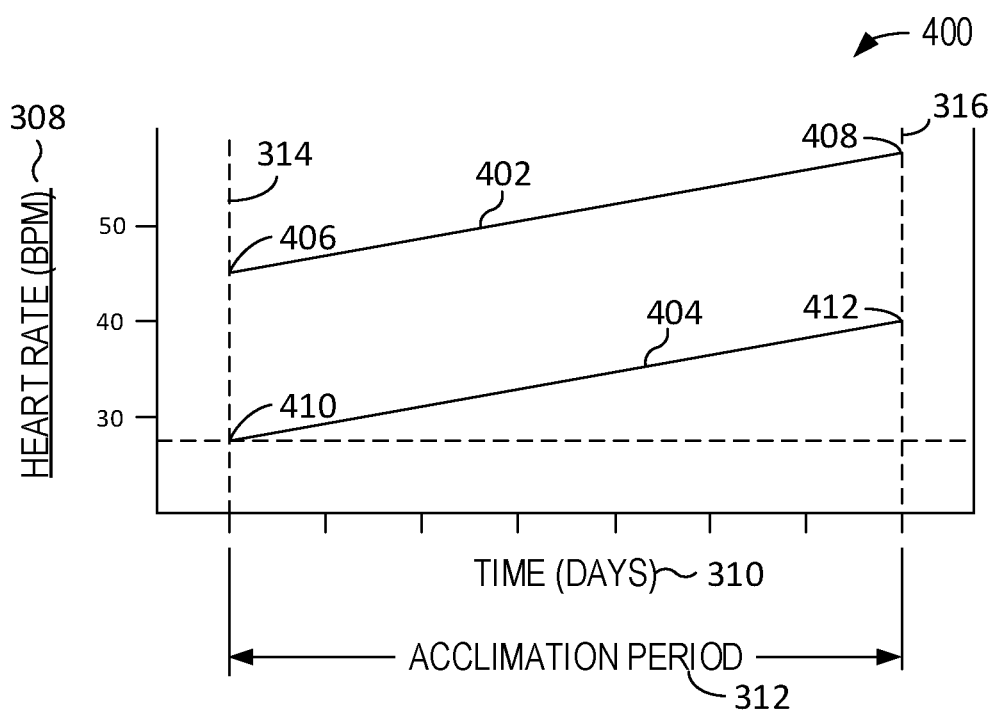
FIG. 4 illustrates an example of a chart depicting an acclimation profile including a daytime acclimation profile and a nighttime acclimation profile, according to an embodiment.

FIG. 4 illustrates an example of a chart 400 depicting a daytime acclimation profile 402 (or active profile or waking profile) and a nighttime (or rest or sleep) acclimation profile 404, according to an embodiment. As previously described with regard to FIG. 3, the chart 400 includes the horizontal axis depicting time 310 and the vertical axis depicting heart rate 308. The daytime acclimation profile 402 and the nighttime acclimation profile 404 can be implemented over the acclimation period 312. In an example, the daytime acclimation profile 402 and the nighttime acclimation profile 404 can be segments of the acclimation profile, such as the acclimation profile 304 or 306.

In some examples, an implantable device can shift from a daytime profile to a nighttime profile (i.e. active profile to resting profile) based on time of day, e.g. the daytime profile can be active from 10 PM to 6 AM and the nighttime profile can be active from 10 PM to 6 AM. In some examples, the time periods that the daytime profile or nighttime profile is active can be programmable by a patient or health care provider or other person involved in patient care. In some examples, the day/active profile can be selected by the implantable device based on sensed activity (e.g. using an accelerometer) or a combination of activity, respiration, time of day, blood pressure, and other sensed parameters. In some examples, the nighttime/resting profile can have a lower LRL to avoid disrupting the patient with a heart rate that is perceived as abnormal, alarming, or distressing. In some examples, the patient can transition into resting profile mode when sleep is detected, which can, for example, allow for daytime napping by a patient or adaption to schedule variations due to travel or other factors, and accordingly avoid disrupting the patient with a heart rate that is perceived as abnormal.

In the example of FIG. 4, the daytime acclimation profile 402 can include a therapy parameter value corresponding to a faster heart rate than the nighttime acclimation profile 404. For instance, where the acclimation profile is based on the LRL, the daytime acclimation profile 402 can include the starting parameter value 406 of fifty-five BPM and a target parameter value 408 of sixty-five BPM. At a programmed time of day, for example, 10:00 pm, the acclimation profile can cycle to the nighttime acclimation profile 402 having a starting parameter value of forty BPM and a target parameter value of fifty-five BPM. Accordingly, the acclimation profile can provide the patient 108 with stimulation therapy that adjusts to a slower pacing rate during nighttime as the patient can be accustomed to a lower heart rate while trying to sleep. For instance, the lower nighttime heart rate can provide a more natural feeling to the patient 108 during the night. The terms daytime and nighttime as used in this specification can refer to any time periods during the twenty-four hour clock and are not limited strictly to day and night. For instance, wake and sleep times can be defined by the patient 108 or the physician to correspond with wake and sleep cycles of the patient 108. The daytime acclimation profile 402 can correspond to the wake cycle and the nighttime acclimation profile 404 can correspond with the sleep cycle.

Figure 5:
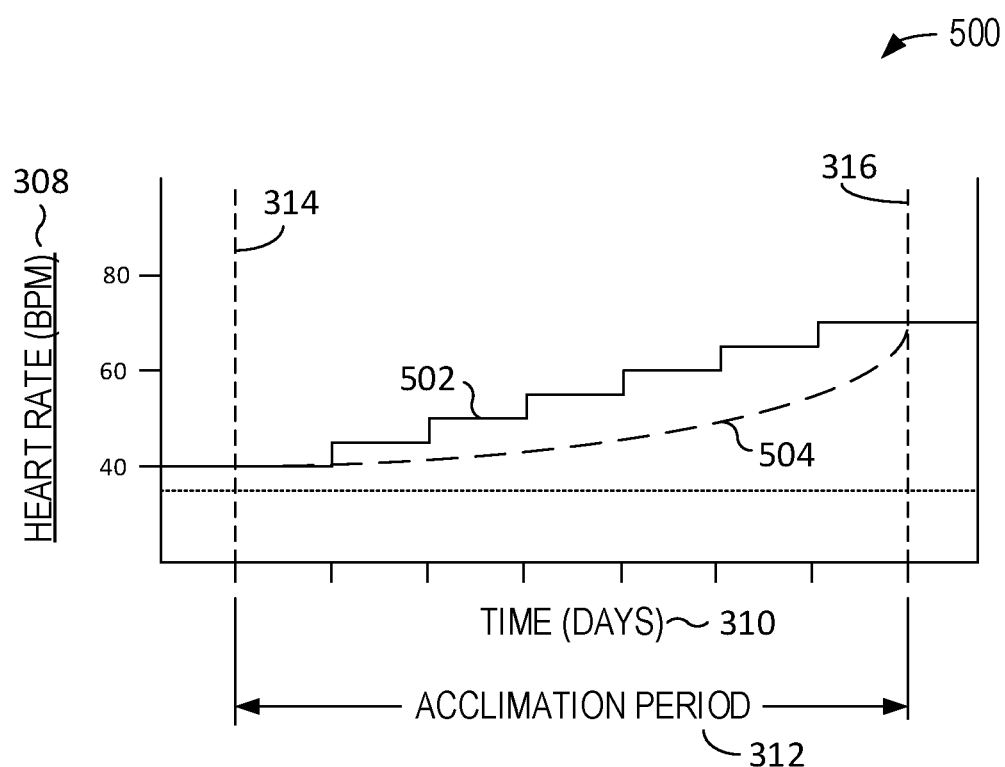
FIG. 5 illustrates an example of a chart depicting further examples of acclimation profiles, according to an embodiment.

FIG. 5 is an illustration 500 of further examples of acclimation profiles, such as acclimation profiles 502 and 504, according to an embodiment. The chart 500 can include the vertical axis depicting heart rate 308, the horizontal axis depicting time 310, and the acclimation period 312 between the starting time 314 and the completion time 314. The acclimation profile can include any profile shape, but typically trends over time from a lower value to a higher value. Several examples are shown for the purpose of illustration in FIG. 5. For instance, the acclimation profile can include a step-wise function as shown in the example of acclimation profile 502. In a further example, the acclimation profile can include a parabolic function as shown in the example of acclimation profile 504. In other examples, the acclimation profile can include exponential, logarithmic, or other profile shapes.

Figure 6:
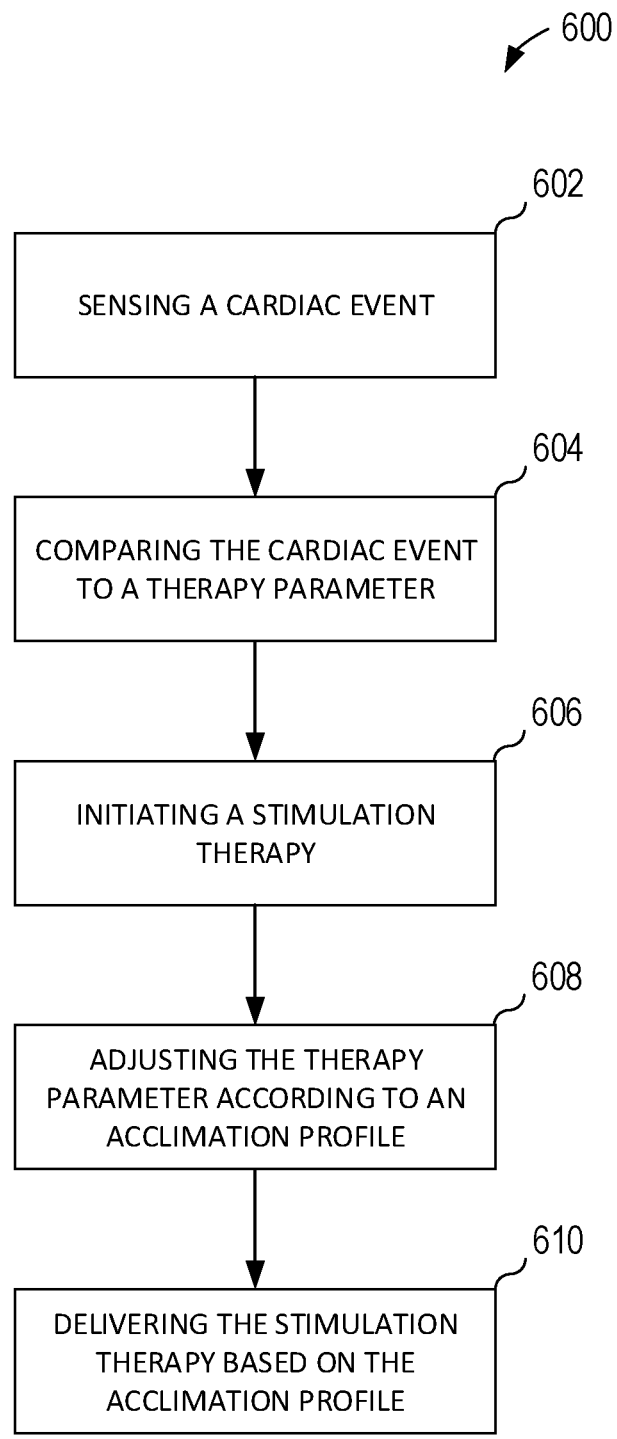
FIG. 6 illustrates an example method for operating an implantable medical device, according to an embodiment.

FIG. 6 is an example of a method 600 for operating an implantable medical device, such as the implantable medical device 102 (e.g., cardiac device) previously described in the examples herein and shown for instance in FIGS. 1 and 2. In describing the method 600, reference is made to one or more components, features, functions, and processes previously described herein. Where convenient, reference is made to the components, features, processes and the like with reference numerals. Reference numerals provided are exemplary and are nonexclusive. For instance, features, components, functions, processes, and the like described in the method 600 include, but are not limited to, the corresponding numbered elements provided herein. Other corresponding features described herein (both numbered and unnumbered) as well as their equivalents are also considered.

At 602, a cardiac event or activity level (e.g., MV) can be sensed. For instance, the cardiac event can be sensed with a sensing circuitry, such as the sensing circuitry 202. As previously discussed, the sensing circuitry can be communicatively coupled to an electrical sensor, pressure transducer, temperature sensor, audio transducer, or other sensor. Accordingly, the sensing circuitry can detect the cardiac event. In an example, the cardiac event can include, but is not limited to, a P wave, QRS wave, other cardiac electrical activity, a change in arterial or ventricular pressure, change in temperature, change in breathing, or other physiological characteristics of the patient. In an example, a controller, such as controller 204, can detect the cardiac event sensed by the sensing circuitry.

At 604, the cardiac event can be compared to a therapy parameter. For instance, the activity level is used to determine the prescribed heart rate. In an example, the cardiac event or other physiological characteristic sensed from the sensing circuitry can be compared to a threshold, such as the therapy parameter. In an example, the therapy parameter can include the LRL, MTR, RRF, or other parameter as previously described herein. Accordingly, the controller can monitor the patient for treatable symptoms, such as bradycardia, sick sinus syndrome, CI, or the like. For instance, the controller can monitor the heart rate of a patient and compare the heart rate of the patient to at least one therapy parameter.

At 606, a stimulation therapy can be initiated. For instance, when the physiological characteristic exceeds (or drops below) the threshold of the therapy parameter, the stimulation therapy can be initiated by the controller. In an example, the therapy parameter can be the LRL of the implantable medical device. The LRL at a given period of time along the acclimation profile, such as the starting parameter value, can be forty BPM. When the intrinsic heart rate of a patient falls below forty BPM, the stimulation therapy can be initiated.

At 608, the therapy parameter can be adjusted according to an acclimation profile. In an example, the acclimation profile can include a starting parameter value and a target parameter value. The acclimation profile can adjust the therapy parameter over the acclimation period. For instance, the acclimation profile can adjust the therapy parameter from the starting parameter value to the target parameter value. The acclimation period can include less than one-day, one day, two days, one week, two weeks, one month, or other time period. For instance the acclimation period can be between one-second and two days. In a further example, the acclimation period can be at least 12 hours, such as between 12 hours and 48 hours. In various examples, the acclimation profile can adjust the therapy parameter by increasing the therapy parameter from the starting parameter value to the target parameter value linearly, step-wise, exponentially, logarithmically, or by another non-linear profile shape. In a further example, the acclimation profile can adjust the therapy parameter based on a percentage of the therapy parameter, such as a percentage of the target parameter value as previously described herein. In some examples, adjusting the therapy parameter can include adjusting the therapy parameter based on a daytime (active) acclimation profile segment and a nighttime (resting) acclimation profile segment. The daytime acclimation profile segment having a therapy parameter corresponding to a faster cardiac rhythm than the nighttime acclimation profile segment. In other examples, a second therapy parameter can be adjusted based on a second acclimation profile. The second acclimation profile can have a second starting parameter value and a second target parameter value. For instance, the controller can adjust the LRL and the MTR or other combinations of therapy parameters, such as those described herein.

At 610, the stimulation therapy can be delivered based on the acclimation profile. For instance the stimulation therapy can be initiated by the controller and delivered to the patient by the pulse generation circuitry, such as pulse generation circuitry 206. In an example, the stimulation therapy can include delivering electrical pulses to a heart of a patient. The electrical pulses can be delivered based on the acclimation profile. Accordingly, the stimulation therapy can be adjusted by the acclimation profile based on the therapy parameter. The patient can be acclimated the stimulation therapy gradually to reduce alarm, distress, or abnormal sensations that may be experienced by the patient, especially for recently initiated therapy, such as new implants or new therapy parameter values.

Figure 7:
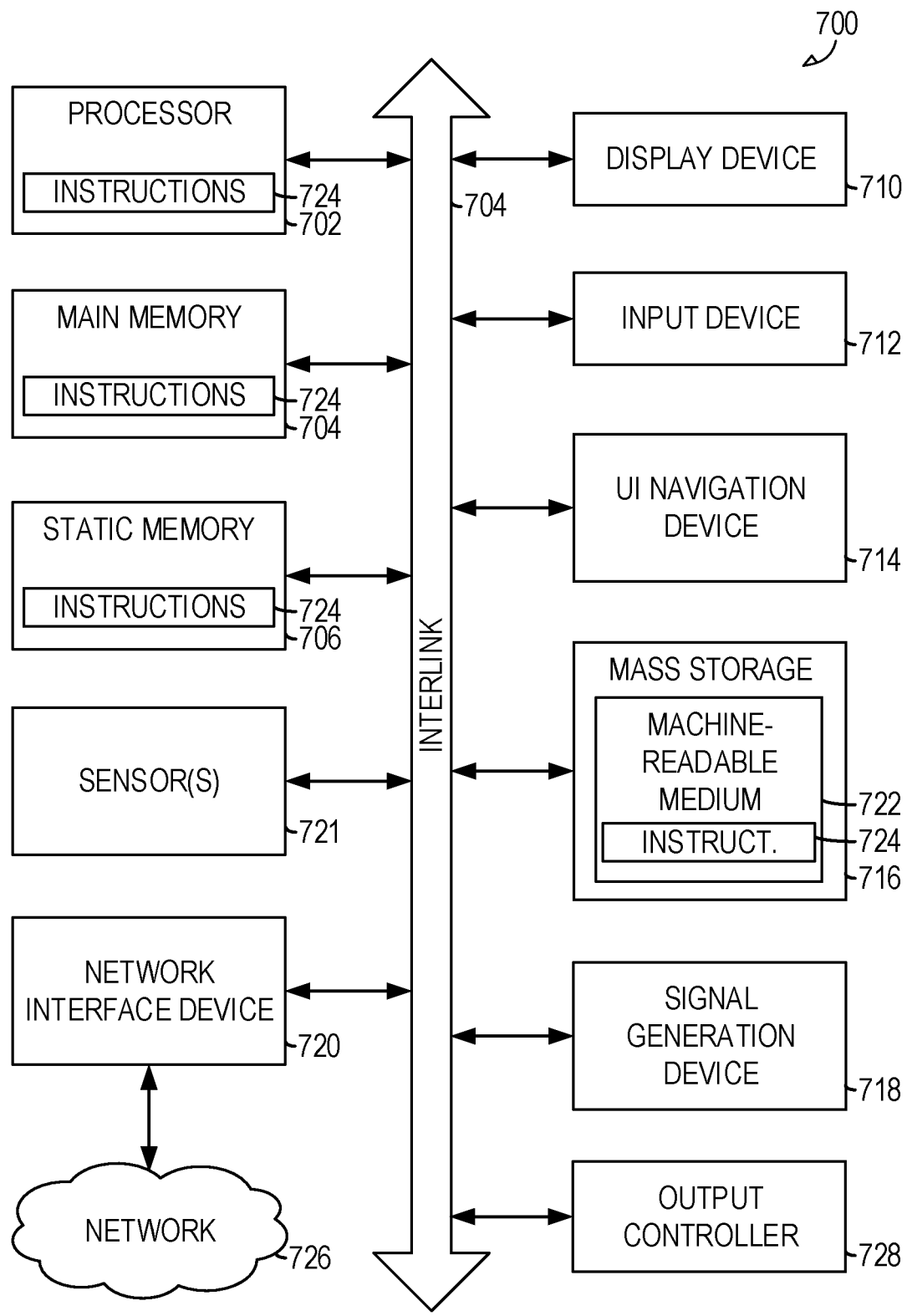
FIG. 7 illustrates a block diagram of an example machine upon which any one or more of the techniques (e.g., methodologies) discussed herein may perform.

FIG. 7 illustrates a block diagram of an example machine 700 upon which any one or more of the techniques (e.g., methodologies) discussed herein may perform. Portions of this description may apply to the computing framework of various portions of the implantable medical device, such as implantable medical device 102 or the external system. In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be or include a special purpose implantable or wearable device, personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710 (e.g., a raster display, vector display, holographic display, etc.), an alphanumeric input device 712 (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensor. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine readable media.

While the machine readable medium 722 is illustrated as a single medium, the term "machine readable medium" may include a single medium or multiple media (e.g., a centralized or distributed database, and/or associated caches and servers) configured to store the one or more instructions 724.

The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may further be transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

Various embodiments are illustrated in the figures above. One or more features from one or more of these embodiments may be combined to form other embodiments.

Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A method of operating a cardiac device, comprising:
    initiating delivery of a stimulation therapy to a heart of a patient, the stimulation therapy including delivering electrical pulses to the heart of the patient based on a therapy parameter; and adjusting the therapy parameter according to an acclimation profile to acclimate the patient to the delivery of the stimulation therapy, wherein adjusting the therapy parameter includes adjusting the therapy parameter based on a daytime acclimation profile segment and a nighttime acclimation profile segment, the daytime acclimation profile segment having a therapy parameter corresponding to a faster cardiac rhythm than the nighttime acclimation profile segment.

2. The method of claim 1, wherein the acclimation profile includes adjusting the therapy parameter from a starting parameter value to a target parameter value over an acclimation period.

3. The method of claim 2, wherein adjusting the therapy parameter includes adjusting the therapy parameter from the starting parameter value to the target parameter value along the acclimation profile linearly.

4. The method of claim 2, wherein adjusting the therapy parameter includes adjusting at least one of the starting parameter value and the target parameter value are based on a percentage of the therapy parameter.

5. The method of claim 2, further comprising adjusting a second therapy parameter based on a second acclimation profile having a second starting parameter value and a second target parameter value.

6. The method of claim 1, wherein adjusting the therapy parameter includes adjusting the therapy parameter during an acclimation period that extends for at least 12 hours.

7. The method of claim 1, wherein adjusting the therapy parameter includes adjusting a lower rate limit of a cardiac rhythm.

8. The method of claim 1, wherein adjusting the therapy parameter includes adjusting a maximum tracking rate of a cardiac rhythm.

9. The method of claim 1, wherein adjusting the therapy parameter includes adjusting a rate response factor, the rate response factor is a rate at which a cardiac rhythm is adjusted by pulse generation circuitry.

10. An implantable medical device comprising:
pulse generation circuitry for generating electrical pulses to provide a stimulation therapy to a heart of a patient;
sensing circuitry for sensing cardiac electrical activity; and
a controller for detecting cardiac events that define pacing timing intervals and for controlling delivery of electrical pulses in accordance with a programmed mode, wherein the controller is programmed to:
provide instructions to the pulse generation circuitry to deliver electrical pulses to the heart of the patient, the electrical pulses based on a therapy parameter, wherein the controller is configured to adjust the therapy parameter according to an acclimation profile to acclimate the patient to the stimulation therapy, wherein the acclimation profile includes a daytime acclimation profile segment and a nighttime acclimation profile segment, the daytime acclimation profile segment having a therapy parameter corresponding to a faster cardiac rhythm than the nighttime acclimation profile segment.

11. The implantable medical device of claim 10, wherein the acclimation profile includes a starting parameter value and a target parameter value, wherein the therapy parameter is adjusted from the starting parameter value to the target parameter value over an acclimation period.

12. The implantable medical device of claim 11, wherein the acclimation profile is linear from the starting parameter value to the target parameter value.

13. The implantable medical device of claim 11, wherein the therapy parameter includes is a rate response factor, the rate response factor being a rate at which a cardiac rhythm is adjusted by the pulse generation circuitry, and the acclimation profile includes an adjustment to the rate response factor over the acclimation period.

14. The implantable medical device of claim 11, wherein the acclimation period lasts for at least 12 hours.

15. The implantable medical device of claim 10, wherein the controller is further programmed to adjust a second therapy parameter according to a second acclimation profile.

16. The implantable medical device of claim 11, wherein at least one of the starting parameter value and the target parameter value are based on a percentage of the therapy parameter.

17. The implantable medical device of claim 10, wherein the therapy parameter is a lower rate limit of a cardiac rhythm.

18. The implantable medical device of claim 10, wherein the therapy parameter is a maximum tracking rate of a cardiac rhythm.

* * * * *